United States Patent
Bonrath et al.

(10) Patent No.: US 9,718,749 B2
(45) Date of Patent: Aug. 1, 2017

(54) PROCESS FOR THE PREPARATION OF 3,7-DIMETHYLNONAN-1-OL

(71) Applicant: DSM IP ASSETS B. V., Heerlen (NL)

(72) Inventors: Werner Bonrath, Basel (CH); Jonathan Medlock, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/774,976

(22) PCT Filed: Mar. 11, 2014

(86) PCT No.: PCT/EP2014/054732
§ 371 (c)(1),
(2) Date: Sep. 11, 2015

(87) PCT Pub. No.: WO2014/140032
PCT Pub. Date: Sep. 18, 2014

(65) Prior Publication Data
US 2016/0023976 A1    Jan. 28, 2016

(30) Foreign Application Priority Data

Mar. 13, 2013 (EP) .................................... 13158908

(51) Int. Cl.
| C07C 45/51 | (2006.01) |
| C07C 29/14 | (2006.01) |
| C07C 29/141 | (2006.01) |
| C07C 29/17 | (2006.01) |
| C07C 29/136 | (2006.01) |
| C11B 9/00 | (2006.01) |
| A23L 27/20 | (2016.01) |

(52) U.S. Cl.
CPC ........ *C07C 29/175* (2013.01); *A23L 27/2026* (2016.08); *C07C 29/136* (2013.01); *C07C 29/14* (2013.01); *C07C 29/141* (2013.01); *C07C 29/172* (2013.01); *C07C 45/51* (2013.01); *C07C 45/511* (2013.01); *C07C 45/512* (2013.01); *C07C 45/515* (2013.01); *C11B 9/0015* (2013.01)

(58) Field of Classification Search
CPC ..... C07C 45/51; C07C 45/511; C07C 45/512; C07C 45/515
See application file for complete search history.

(56) References Cited

U.S. PATENT DOCUMENTS

| 2,815,379 A | 12/1957 | Surmatis et al. |
| 4,029,709 A | 6/1977 | DeSimone et al. |
| 6,198,006 B1 * | 3/2001 | Bonrath ................ C07C 45/512 568/449 |

FOREIGN PATENT DOCUMENTS

CN         102206137 A    * 10/2011

OTHER PUBLICATIONS

CN 102206137 A, Oct. 2011, pp. 1-5; English translation.*
Pauling, H. et al. Helv. Chim. Acta 1976, 59, pp. 1233-1243.*
Devred, F. et al. Appl. Cat. A: General 2009, 356, pp. 154-161.*
AAAChem (Dec. 16, 2010, pp. 1-5).*
Reyes, P. et al. React. Kinet. Catal. Lett. 2006, 88, pp. 363-369.*
A-4000—Johnson Matthey Fine Chemicals; pp. 1-2.*
International Search Report for PCT/EP2014/054732, mailed Jul. 14, 2014, 3 pages.
Shibata et al., Syntheses of Racemic and Diastereomeric Mixtures of 3,7,11,15-Tetramethylhentriacontane and 4,8,12,16-Tetramethyldotriacontane, the Cuticular Tetramethylalkanes of the Tsetse Fly, *Bioscience, Biotechnology, and Biochemistry*, vol. 66, No. 3, Jan. 11, 2002, pp. 585-587.
Miller et al., Stereoselective syntheses of isomers of 3,7-dimethylnonadecane, a sex pheromone of the alfalfa blotch leafminer (Agromyza frontella (Rondani)), *Canadian Journal of Chemistry*, Jul. 1, 1991, pp. 1100-1106.
Suzuki et al., Synthesis of optically active aggregation pheromone analogues of the red flour beetle, Tribolium castaneum, *Agricultural and Biological Chemistry*, vol. 47, No. 4, Jan. 1, 1983, pp. 869-875.

* cited by examiner

*Primary Examiner* — Medhanit Bahta
(74) *Attorney, Agent, or Firm* — Nixon & Vanderhye P.C.

(57) ABSTRACT

The present invention is related to a novel and improved process for the preparation of 3,7-dimethylnonan-1-ol.

14 Claims, No Drawings

PROCESS FOR THE PREPARATION OF 3,7-DIMETHYLNONAN-1-OL

This application is the U.S. national phase of International Application No. PCT/EP2014/054732 filed 11 Mar. 2014 which designated the U.S. and claims priority to EP Patent Application No. 13158908.7 filed 13 Mar. 2013, the entire contents of each of which are hereby incorporated by reference.

The present invention is related to a novel and improved process for the preparation of 3,7-dimethylnonan-1-ol.

3,7-dimethylnonan-1-ol (compound of formula (I)), also known as ethyltetrahydrogeraniol (E-THGOL) can be used in the field of flavour and fragrance applications.

3,7-dimethylnonan-1-ol is a known compound (CAS 86414-50-8). I.e. it is described in Biosci. Biotechnol. Biochem., 66(2), 2002, P. 582-587.

The goal of the present invention was to find a synthesis which is easier (i.e. less steps) and which leads to excellent yields and high conversion.

The newly found process for the preparation of E-THGOL is a two-step process starting from 3,7-dimethylnon-6-en-1-yn-3-ol (compound of formula (II)) via 3,7-dimethylnona-2,6-dienal (compound of formula (III)).

3,7-dimethylnon-6-en-1-yn-3-ol (compound of formula (II)), which is the starting material is a known compound and is available commercially. It could also be produced according to methods described in the prior art (i.e. WO2004/018400).

3,7-dimethylnona-2,6-dienal, also known as E-citral, can also be used in the field of flavour and fragrance applications.

The yields and the conversion of the products of both steps are excellent. The E/Z isomerism (geometric isomerism) of compound of formula (II) as well as of compound of formula (III) is not crucial for the reactions. The compound of formula (II) as well as the compound of formula (III) can be a single isomeric form as well as mixtures of isomeric forms.

The new process according to the present invention is the following:

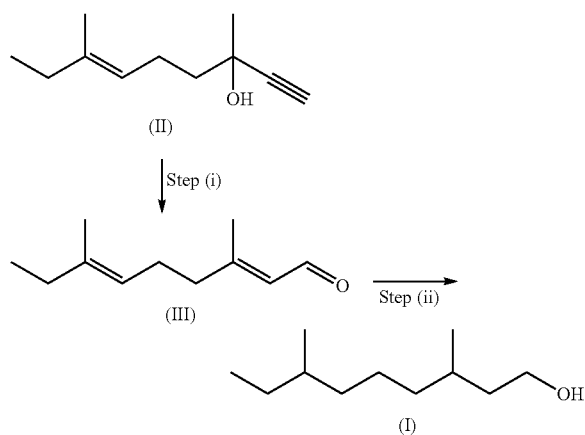

Step (i):

This reaction is a rearrangement reaction using a catalyst. Such a rearrangement is known from the prior art (i.e. Helvetica Chimica Acta, Vol. 59. Fasc. 4, P. 1233-1243 (1976).

This reaction is carried out in aliphatic and/or aromatic hydrocarbons as solvents. A single solvent as well as a mixture of solvents can be used. Preferably high boiling hydrocarbons are used.

Examples of such solvents are paraffin oil, hexane, xylene.

The reaction of step (i) is usually carried out at an elevated temperature. Usually at a temperature of at least 50° C. Preferably the reaction of step (i) is carried out at a temperature of 50 to 200° C.

The reaction of step (i) is usually carried out at normal pressure. It could also be carried out at lower or higher pressure.

The reaction of step (i) is usually carried out in the presence of a catalyst. Preferred is a catalyst, which is a compound of formula (IV)

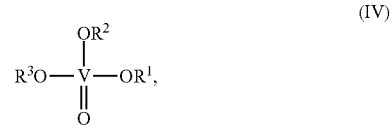

wherein $R^1$, $R^2$ and $R^3$ are independently from each other a linear or branched $C_1$-$C_{10}$-alkyl moiety or $Si(R^4)_3$, wherein each $R^4$ is independently from each other a linear or branched $C_1$-$C_{10}$-alkyl moiety or substituted or unsubstituted phenyl. Preferred is a catalyst of formula (IV), wherein $R^1$, $R^2$, and $R^3$ have all the same meaning.

More preferred is a catalyst of formula (IV), wherein $R^1$, $R^2$, and $R^3$ have all the same meaning and wherein $R^1$, $R^2$, and $R^3$ are linear or branched $C_1$-$C_4$-alkyl moiety or $Si(R^4)_3$, wherein each $R^4$ is a linear or branched $C_1$-$C_4$-alkyl moiety or substituted or unsubstituted phenyl.

Most preferred as a catalyst is a catalyst of formula (IV')

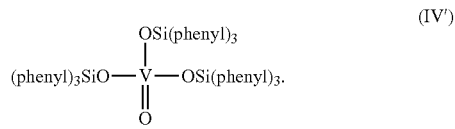

At the end of the reaction the product is removed from the reaction mixture by distillation. Usually a vacuum distillation is used.

Step (ii):

This step is a hydrogenation reaction.

Usually the hydrogenation is carried out by using $H_2$-gas.

It is possible (and preferred) to use pure $H_2$-gas, but it would also be possible to use a gas mixture which comprises $H_2$.

Therefore the present invention relates to a process as described above wherein the hydrogenation is carried out by using (pure) $H_2$-gas.

The hydrogenation is usually carried out under pressure. The pressure is preferably at least 1.5 bar. Usually not more than 50 bar is used. A preferred range for the pressure is 1.5-40 bar, more preferably 2-30 bar.

The hydrogenation is usually carried out in a vessel, which is suitable to enduring the pressure.

The hydrogenation is carried out in the presence of a metal catalyst, preferably in the presence of a nickel catalyst.

The nickel catalyst used in the process according to the present invention is a heterogeneous catalyst.

Preferred catalysts are nickel alloy catalysts. Such catalysts are also known as "skeletal catalysts" or "sponge-metal catalysts".

Such catalysts are commercially available for example under the trade name Actimet® from BASF (i.e. Actimet M) or under the product name B 111W, B 112, B 113 W, B 113 Z from Evonik or JM A4000, JM A40A9, JM A2000 from Johnson Matthey Catalysts or Acticat® from CatAlloy (i.e. Acticat 1000, Acticat 1100, Acticat 1200, Acticat 1600).

The catalyst can be reused for further hydrogenation reactions and the catalyst can also be easily recycled.

Usually the catalyst can be used without further treatment. So it is possible to run the hydrogenation batch-wise or continuously.

The ratio (related to the weight) of E-citral to the catalyst in the hydrogenation reaction mixture is usually at least 5:1.

The hydrogenation of E-citral is carried out in a solvent (or solvent mixture) or without using any solvents.

In other words, one embodiment of the present application is a solvent free hydrogenation in step (ii). Solvent free means without the usual amounts of such compounds. It is meant that no solvent is added to the starting materials.

But it is possible that some of the materials used in the hydrogenation may comprise traces of a solvent, which can originate from their production. But the amount of such impurities is small, less than 10% and generally less than 2%.

A solvent or a mixture of solvents can also be used for the hydrogenation in step (ii). Suitable solvents are linear, branched or cyclic aliphatic hydrocarbons having 5-10 carbon atoms; aromatic hydrocarbons having 5-10 carbon atoms; esters; ethers and alcohols.

It is preferred that solvents are used which are liquid under normal conditions, which allows an easy handling.

Preferred solvents are tetrahydrofuran (THF), n-hexane, n-heptane, 2-propanol, toluene and ethyl acetate.

Therefore the present invention relates to a process (A) for the preparation of 3,7-dimethylnonan-1-ol (compound of formula I)

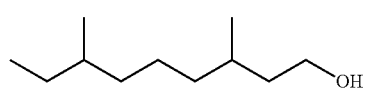

(I)

characterised in that in a first step (i)
a compound of formula (II)

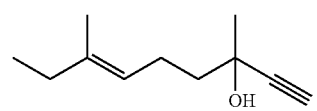

(II)

is submitted to a rearrangement reaction, wherein compound of formula (III) is obtained

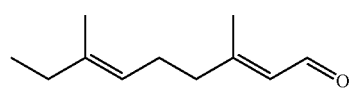

(III)

and in a second step (ii)

the compound of formula (III) is reduced to the compound of formula (I) by using a metal catalyst.

The invention also relates to a process (B), which is a process (A), wherein step (i) a catalyst of formula (IV)

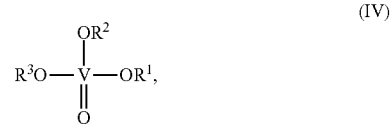

(IV)

wherein $R^1$, $R^2$ and $R^3$ are independently from each other a linear or branched $C_1$-$C_{10}$-alkyl moiety or $Si(R^4)_3$, wherein each $R^4$ is independently from each other a linear or branched $C_1$-$C_{10}$-alkyl moiety or substituted or unsubstituted phenyl, is used.

The invention also relates to a process (B'), which is a process (B), wherein step (i) a catalyst of formula (IV) is used, wherein $R^1$, $R^2$, and $R^3$ have all the same meaning and wherein $R^1$, $R^2$, and $R^3$ are linear or branched $C_1$-$C_4$-alkyl moiety or $Si(R^4)_3$, wherein each $R^4$ is a linear or branched $C_1$-$C_4$-alkyl moiety or substituted or unsubstituted phenyl.

The invention also relates to a process (B"), which is a process (B), wherein step (i) a catalyst of formula (IV')

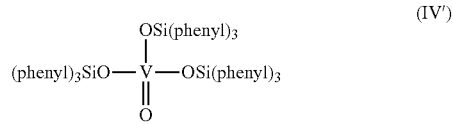

(IV')

is used.

The invention also relates to a process (C), which is a process (A), (B), (B') or (B"), wherein step (i) the reaction is carried out in at least one hydrocarbon as solvent.

The invention also relates to a process (D), which is a process (A), (B), (B'), (B") or (C), wherein step (i) the reaction is carried out in at least one hydrocarbon chosen from the group consisting of paraffin oil, hexane and xylene The invention also relates to a process (E), which is a process (A), (B), (B'), (B"), (C) or (D), wherein step (i) the reaction is carried out at a temperature of 50° C. to 200° C.

The invention also relates to a process (F), which is a process (A), (B), (B'), (B"), (C), (D) or (E), wherein step (i) the reaction is carried out at out at normal pressure.

The invention also relates to a process (G), which is a process (A), (B), (B'), (B"), (C), (D), (E) or (F), wherein step (ii) pure $H_2$-gas or a gas mixture which comprises $H_2$ is used.

The invention also relates to a process (H), which is a process (A), (B), (B'), (B"), (C), (D), (E), (F) or (G), wherein step (ii) the hydrogenation is carried out at a pressure of 1.5-40 bar, more preferably 2-30 bar.

The invention also relates to a process (I), which is a process (A), (B), (B'), (B"), (C), (D), (E), (F), (G) or (H), wherein step (ii) is carried out in the presence of a nickel catalyst.

The invention also relates to a process (J), which is a process (A), (B), (B'), (B"), (C), (D), (E), (F), (G), (H) or (I), wherein step (ii) is carried out in the presence of a heterogeneous nickel catalyst.

The invention also relates to a process (K), which is a process (A), (B), (B'), (B"), (C), (D), (E), (F), (G), (H), (I) or (J), wherein step (ii) is carried out without using any solvents.

The invention also relates to a process (L), which is a process (A), (B), (B'), (B"), (C), (D), (E), (F), (G), (H), (I) or (J), wherein step (ii) is carried out in a solvent or a solvent mixture.

The invention also relates to a process (M), which is a process (A), (B), (B'), (B"), (C), (D), (E), (F), (G), (H), (I), (J) or (L), wherein in step (ii) is carried out in at least one solvent chosen from the group consisting of linear, branched or cyclic aliphatic hydrocarbons having 5-10 carbon atoms; aromatic hydrocarbons having 5-10 carbon atoms; esters; ethers; alcohols.

The invention also relates to a process (N), which is a process (A), (B), (B'), (B"), (C), (D), (E), (F), (G), (H), (I), (J), (L) or (M), wherein in step (ii) is carried out in at least one solvent chosen from the group consisting tetrahydrofuran (THF), n-hexane, n-heptane, 2-propanol, toluene and ethyl acetate.

Furthermore, the invention also relates to the use of a compound of formula (I) in flavour and/or fragrance applications.

Furthermore, the invention also relates to the use of a compound of formula (II) in flavour and/or fragrance applications.

The following examples serve to illustrate the invention. If not otherwise stated all parts are given are related to the weight and the temperature is given in ° C.

EXAMPLES

Example 1—Preparation of 3,7-dimethylnona-2,6-dienal

Ethyl-dehydrolinalool (3,7-dimethylnon-6-en-1-yn-3-ol, 27.4 g), stearic acid (465 mg), triphenylsilanol (5.87 g), tris-(triphenylsiloxy)-vanadiumoxide (2.95 g) and paraffin oil (163 g) were placed in a 350 ml four-necked flask. With the oil bath (Temperature 145° C.), the mixture was heated up under a slight argon overflow. An internal temperature of ~138° C. was reached and the reaction mixture was stirred for a total of five hours. The reaction mixture was cooled down to a TI of ~70° C. and distillation equipment was installed on the reaction flask. The product including unconverted ethyl-dehydrolinalool was distilled at a head temperature of up to 59° C. at 0.05-0.08 mbar. After approximately 1 h, the distillation was completed. The product was analyzed by GC with internal standard. (hexadecane)

A clear slightly yellow oil (28.1 g) was isolated.

GC analysis showed 0.96 w % unconverted ethyl-dehydrolinalool and 88.9 w % of four ethyl-citral isomers. Conversion: 99.0%, yield 92.2%.

Example 2a—Preparation of 3,7-dimethylnonan-1-ol

The nickel catalyst (Johnson Matthey A4000, 250 mg) was added to a 100 ml reactor fitted with a gas entrainment stirrer. The catalyst was washed with 3× anhydrous ethanol and 2× heptane. 3,7-Dimethylnona-2,6-dienal (5.0 g) and the heptane (40 g) were added and the autoclave was sealed. The reactor was purged 5 times with nitrogen and 5 times with hydrogen. The reactor was heated to 80° C. and then pressurized to 20 bar with hydrogen. The reaction mixture was stirred for 20 hours. At the end of the reaction the reactor was cooled to room temperature, the pressure released and purged once with nitrogen. The reaction mixture was filtered and analysed by GC for conversion and selectivity. Yield: 5.0 g of a colourless oil conversion>99%, product 98.5%.

1H NMR: 3.77-3.61 (2H, m), 1.70-1.48 (2H, m), 1.47-1.00, 11H, m) and 0.94-0.81 (9h, m)

Mass spectrum: 154 (M-$H_2O$), 139, 125, 97, 83, 70, 55, 41, 29

IR (cm$^{-1}$): 3324 (br), 2957, 2925, 2872, 1461, 1377

Example 2b—Preparation of 3,7-dimethylnonan-1-ol

In a similar way to example 2a, 3,7-dimethylnona-2,6-dienal (5.0 g), ethyl acetate (40 g) and the nickel catalyst (Johnson Matthey A4000, 250 mg) were reacted at 80° C., 20 bar hydrogen for 20 hours. Yield: 5.00 g of a colourless oil, conversion>99%, product 98.9%.

Example 3—Preparation of 3,7-dimethylnonan-1-ol, solvent-free

The nickel catalyst (1 g) was added to a 100 ml reactor fitted with a gas entrainment stirrer. The catalyst was washed with anhydrous ethanol and ethyl acetate. E-citral (3,7-dimethylnona-2,6-dienal, 40 g) was added and the reactor was sealed. The reactor was purged 5 times with nitrogen and 5 times with hydrogen. The reactor was heated to 80° C. and then pressurized to 20 bar with hydrogen. The reaction mixture was stirred for 30 hours. At the end of the reaction the reactor was cooled to room temperature, the pressure released and purged once with nitrogen. The reaction mixture was filtered and analysed by GC for conversion and selectivity. Yield: 39.29 g of a colourless oil, conversion>99%, product 98.6%.

The invention claimed is:

1. A two-step process for the production of a compound of formula (I):

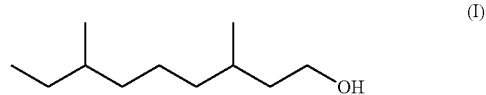

(I)

wherein
the process consists of:
(i) subjecting in a first step a compound of formula (II):

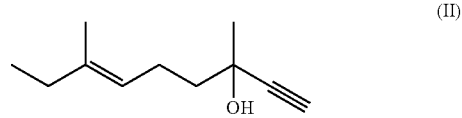

(II)

to a rearrangement reaction to obtain a compound of formula (III);

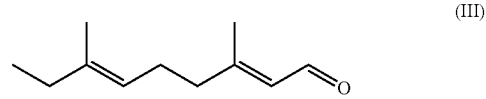

(III)

and thereafter (ii) subjecting in a second step the compound of formula (III) to hydrogenation in the presence of a nickel/chromium catalyst with Fe/Cr promoter to obtain the compound of formula (I) with a conversion of greater than 99%.

2. The two-step process according to claim 1, which comprises using in step (i) a catalyst of formula (IV):

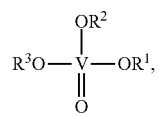

wherein
$R^1$, $R^2$ and $R^3$ are independently from each other a linear or branched $C_1$-$C_{10}$-alkyl moiety or $Si(R^4)_3$, and wherein
each $R^4$ is independently from each other a linear or branched $C_1$-$C_{10}$-alkyl moiety or substituted or unsubstituted phenyl.

3. The two-step process according to claim 1, which comprises using in step (i) a catalyst of formula (IV'):

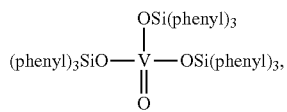

4. The two-step process according to claim 1, wherein the reaction of step (i) is carried out in at least one hydrocarbon solvent.

5. The two-step process according to claim 1, wherein the reaction of step (i) is carried out at a temperature of 50° C. to 200° C.

6. The two-step process according to claim 1, wherein the reaction of step (i) is carried out at normal pressure.

7. The two-step process according to claim 1, wherein step (ii) is carried out using pure $H_2$-gas or a gas mixture which comprises $H_2$.

8. The two-step process according to claim 1, wherein the hydrogenation of step (ii) is carried out at a pressure of 1.5-40 bar.

9. The two-step process according to claim 1, wherein the catalyst of step (ii) is a sponge nickel/chromium catalyst with Fe/Cr promoter.

10. The two-step process according to claim 1, wherein step (ii) is carried out in the absence of solvents.

11. The two-step process according to claim 1, wherein step (ii) is carried out in a solvent or a solvent mixture.

12. The two-step process according to claim 11, wherein the solvent is at least one selected from the group consisting of linear, branched or cyclic aliphatic hydrocarbons having 5-10 carbon atoms; aromatic hydrocarbons having 5-10 carbon atoms; esters; ethers; and alcohols.

13. The two-step process according to claim 12, wherein the solvent is at least one selected from the group consisting tetrahydrofuran (THF), n-hexane, n-heptane, 2-propanol, toluene and ethyl acetate.

14. The two-step process according to claim 8, wherein the hydrogenation of step (ii) is carried out at a pressure of 2-30 bar.

* * * * *